(12) United States Patent
Tekulve

(10) Patent No.: US 9,302,031 B2
(45) Date of Patent: Apr. 5, 2016

(54) TUBULAR DRAINAGE DEVICE

(75) Inventor: Kurt J. Tekulve, Ellettsville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 709 days.

(21) Appl. No.: 13/302,623

(22) Filed: Nov. 22, 2011

(65) Prior Publication Data

US 2013/0131645 A1 May 23, 2013

(51) Int. Cl.
*A61M 27/00* (2006.01)
*A61M 31/00* (2006.01)
*A61M 1/00* (2006.01)

(52) U.S. Cl.
CPC .......... *A61M 1/008* (2013.01); *A61B 2217/005* (2013.01)

(58) Field of Classification Search
CPC ....... A61M 25/00; A61M 2/01; A61M 25/09; A61M 25/10; A61M 27/00; A61M 39/00; A61M 39/10; A61F 5/445
USPC .................. 604/323, 326, 504, 540, 541, 543
See application file for complete search history.

(56) References Cited

U.S. PATENT DOCUMENTS

| 3,416,532 | A | 12/1968 | Grossman |
| 4,813,929 | A | 3/1989 | Semrad |
| 5,279,567 | A | 1/1994 | Ciaglia et al. |
| 5,458,583 | A | 10/1995 | McNeely et al. |
| 5,509,909 | A | 4/1996 | Moy |
| 5,653,230 | A | 8/1997 | Ciaglia et al. |
| 5,897,534 | A | 4/1999 | Heim et al. |
| 6,183,450 | B1 | 2/2001 | Lois |
| 6,517,519 | B1 | 2/2003 | Rosen et al. |
| 6,692,508 | B2 | 2/2004 | Wensel et al. |
| 6,905,484 | B2 | 6/2005 | Buckman et al. |
| 7,036,510 | B2 | 5/2006 | Zgoda et al. |
| 7,229,433 | B2 | 6/2007 | Mullen |
| 7,854,728 | B2 | 12/2010 | Boyle, Jr. |
| 7,951,243 | B2 | 5/2011 | Boyle, Jr. et al. |
| 2004/0133232 | A1 | 7/2004 | Rosenbluth et al. |
| 2006/0081260 | A1 | 4/2006 | Eells et al. |
| 2006/0237022 | A1 | 10/2006 | Chen et al. |

(Continued)

FOREIGN PATENT DOCUMENTS

| GB | 2425483 A | 11/2006 |
| WO | WO 01/12086 A1 | 2/2001 |
| WO | WO 03/080166 A1 | 10/2003 |

OTHER PUBLICATIONS

Extended European Search Report, dated Feb. 28, 2013, pp. 1-6, European Patent Application No. 12193047.3, European Patent Office, The Netherlands.

*Primary Examiner* — Melanie Hand
(74) *Attorney, Agent, or Firm* — Brinks Gilson & Lione

(57) ABSTRACT

A medical device for draining a fluid from the body of a patient includes a tubular member having an open distal end that resides interiorly of the body of a patient and a proximal end that extends exteriorly of the body of the patient. The tubular member has an inner surface extending between the distal end and the proximal end, wherein the inner surface defines a lumen. An interior member is disposed in the lumen and extends along a length of the inner surface. The interior member is engaged with the inner surface such that a chamber is defined therebetween. A conduit is engaged with the tubular member for transmission of an inflation fluid to selectively vary a dimension of the chamber for freeing clogged debris in the lumen.

15 Claims, 3 Drawing Sheets

(56) References Cited

U.S. PATENT DOCUMENTS

| | | |
|---|---|---|
| 2006/0264988 A1 | 11/2006 | Boyle |
| 2008/0171992 A1* | 7/2008 | House ............................ 604/180 |
| 2009/0054805 A1* | 2/2009 | Boyle, Jr. ....................... 600/564 |
| 2009/0188531 A1 | 7/2009 | Boyle, Jr. et al. |
| 2009/0264833 A1 | 10/2009 | Boyle, Jr. |
| 2009/0318898 A1 | 12/2009 | Dein |
| 2011/0040285 A1 | 2/2011 | Boyle |
| 2011/0040286 A1 | 2/2011 | Boyle, Jr. et al. |
| 2011/0152874 A1 | 6/2011 | Lyons |
| 2011/0152920 A1 | 6/2011 | Eckhouse et al. |
| 2012/0017943 A1 | 1/2012 | Boyle, Jr. et al. |

* cited by examiner

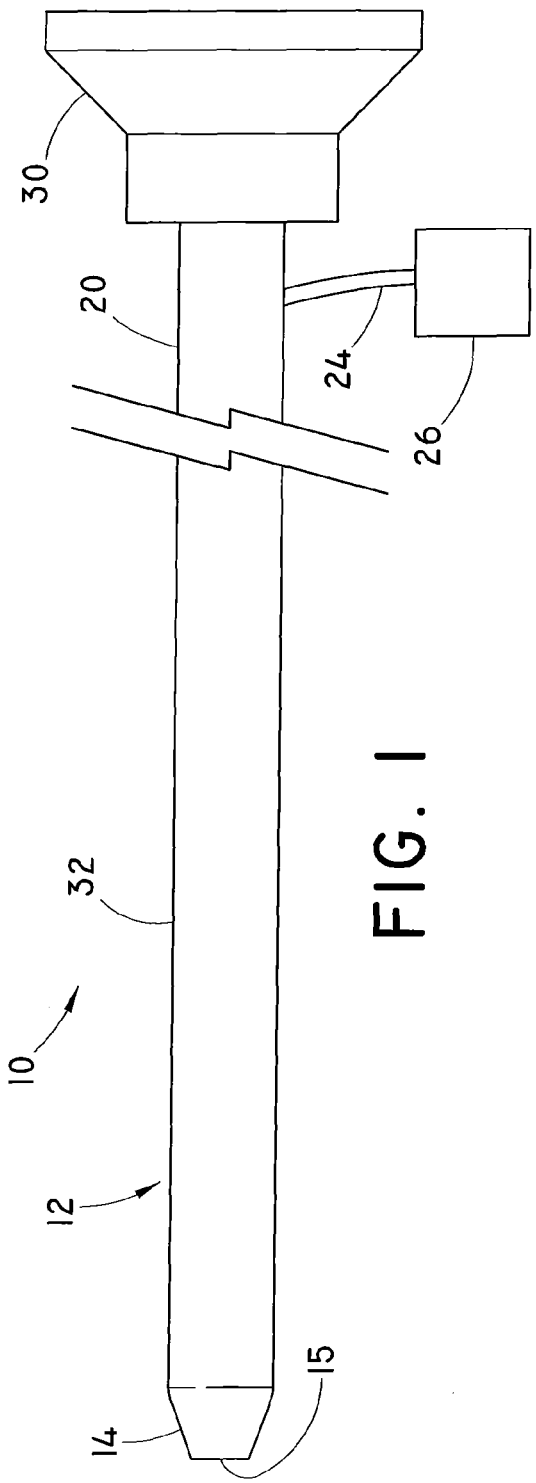
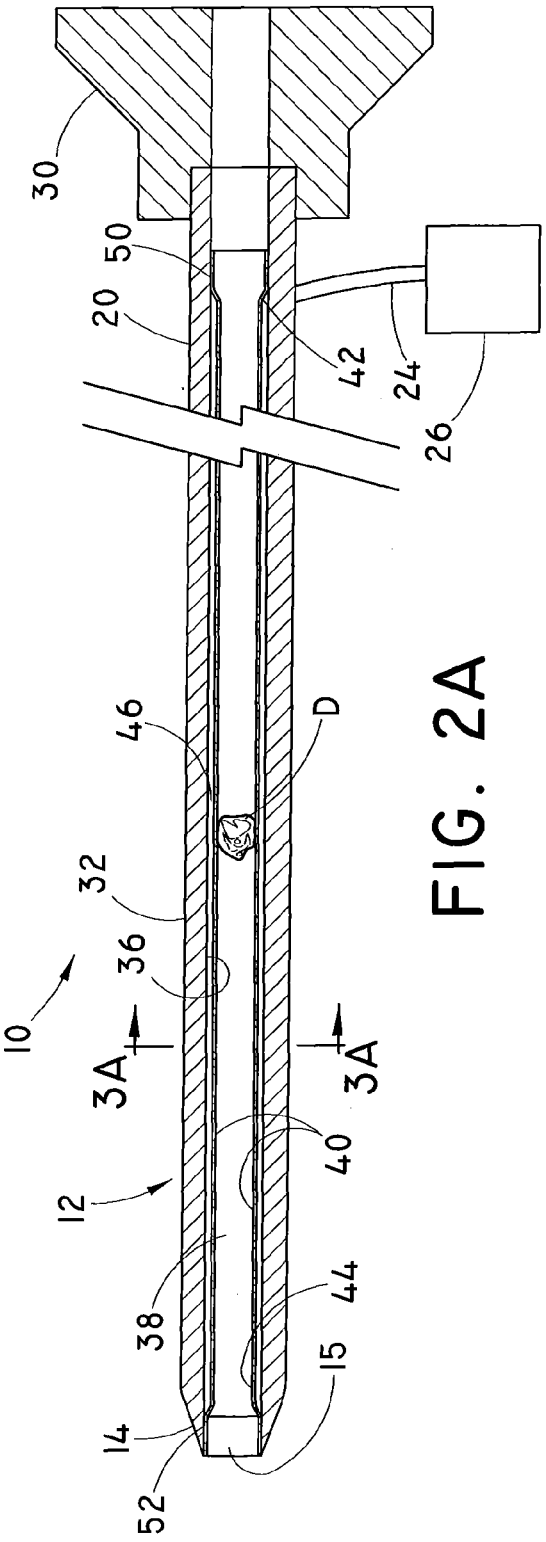

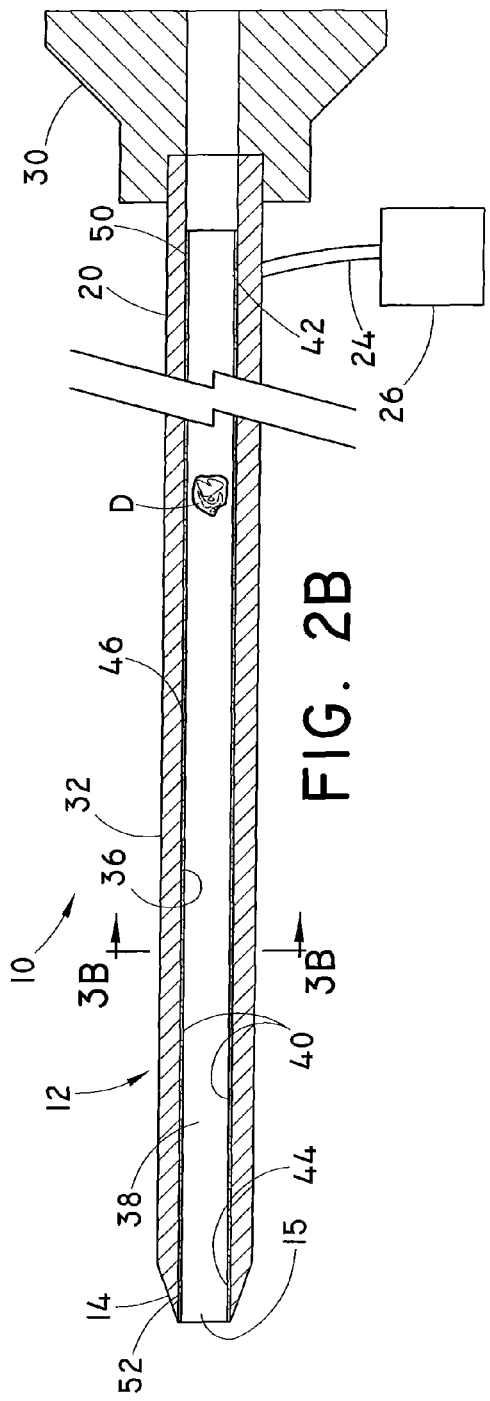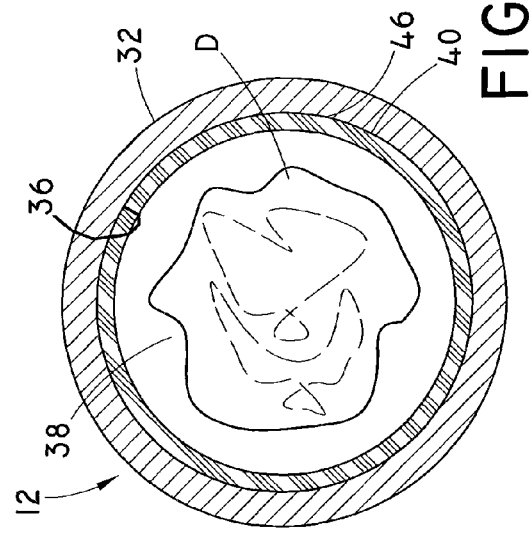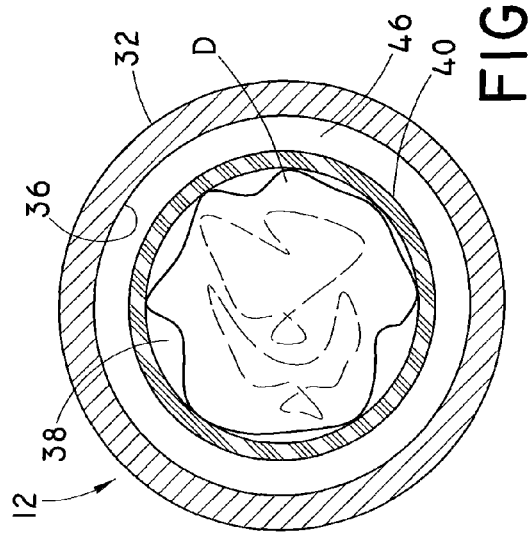

TUBULAR DRAINAGE DEVICE

BACKGROUND

The present disclosure relates generally to the field of medical devices, and more particularly, to a tubular device for use in draining fluids from the body of a patient.

In the human body, the lungs are surrounded by the pleura. The pleura is a serous membrane which folds back upon itself to form a two membrane structure. The two membranes are known as the parietal pleura and the visceral pleura, respectively. The parietal (outer) pleura lines the chest wall, while the visceral (inner) pleura surrounds the lung. The space between the two pleurae layers is known as the pleural space or cavity, which space typically contains a thin layer of pleural fluid. This thin layer of fluid provides lubrication to enable the plurae layers to smoothly slide over one another during respiration.

Pleural effusion refers to a condition that occurs when an excess of fluid accumulates in the pleural space. Typically, such accumulation results from chest trauma experienced by the patient. The collection of air in the pleural space results in a condition commonly referred to as pneumothorax. The collection of blood in the pleural space results in a condition commonly referred to as hemothorax. Other fluids that may collect in the pleural space include serous fluid (hydrothorax), chyle (chylothorax), and pus (pyothorax). The presence of excessive amounts of fluids in the pleural space impairs the breathing ability of the patient by limiting the ability of the lungs to expand during inhalation.

In order to drain excess fluid, a chest tube may be inserted into the pleural space. Often the chest tube is inserted utilizing the well-known Seldinger technique. In the Seldinger technique, a needle is initially advanced into the pleural space. A wire guide is inserted through a bore of the needle, and the needle is thereafter removed, leaving the distal end of the wire guide positioned in the pleural space. A series of tapered dilators (such as three) are sequentially advanced (small to large) over the wire guide to dilate the tissue of the chest wall, and form an opening, or stoma, of desired size. Alternatively, an inflatable balloon may be inserted to dilate the tissue. After removal of the dilator, the chest tube is placed over the wire guide, and the distal end of the tube is directed into the pleural space. Further discussion of the insertion of a chest tube into the pleural space is provided in U.S. Pat. Publ. No. 2011/0152874, incorporated by reference herein.

During drainage of fluid through the chest tube, blood or other fluids can clot or otherwise accumulate in the lumen of the tube. When this occurs, the flow of fluids through the chest tube becomes partially or fully blocked. Consequently, since the fluid cannot fully pass through the tube, excess fluid may build up in the pleural space. The build-up of excess fluid in the pleural space can restrict the full expansion of the lungs and lead to deleterious consequences to the patient, including potential death. When the chest tube is implanted and sterile, the end user can at times manipulate the chest tube to remove a blood clot, etc., such as by squeezing the chest tube, bending the chest tube at several points, and/or sliding while squeezing the chest tube. The chest tube can be partially withdrawn in order to gain external access to the blood clot. However, this action violates the sterile internal environment of the chest tube, making the treated area more susceptible to infection. Further, the seal between the chest tube and the drainage system is broken, which can increase the risk of losing the physiological negative pressure inside the chest.

It would be desirable to provide a drainage device that includes means for effectively eliminating blocking or clogging of the device. It would be desirable if such action occurs while maintaining the drainage device implanted within the patient in order to maintain a sterile environment.

SUMMARY

The present invention addresses the shortcomings of the prior art. In one form, the invention is directed to a medical device for draining a fluid from the body of a patient. The medical device includes a tubular member configured to have a distal end residing interiorly of the body of a patient and a proximal end extending exteriorly of the body of the patient. The distal end has an opening for transmission of the fluid. The tubular member has an inner surface extending between the distal end and the proximal end, wherein the inner surface defines a lumen. An interior member is disposed in the lumen and extends along a length of the inner surface. The interior member is engaged with the inner surface such that a chamber is defined therebetween. A conduit is engaged with the tubular member for transmission of an inflation fluid for selectively varying a dimension of the chamber.

In another form thereof, the invention is directed to a drainage system. The drainage system comprises a tubular member configured to have a distal end residing within an interior body space of a patient and a proximal end extending outside of the body of the patient. The distal end has an opening for receiving a body fluid from the body space. The tubular member has an inner surface extending between the distal end and the proximal end, wherein the inner surface defines a lumen. An interior member is disposed in the lumen and extends along a length of the inner surface. The interior member is engaged with the inner surface such that a substantially air-tight chamber is defined therebetween. A source of an inflation fluid is in communication with the chamber.

In still another form thereof, the invention is directed to a method for draining a body fluid from an interior body space of a patient. A drainage tube is positioned for receiving the body fluid. The drainage tube comprises a tubular member having a distal end residing within the interior body space of the patient and a proximal end extending outside of the body of the patient. The tubular member has an inner surface extending between the distal end and the proximal end, wherein the inner surface defines a lumen. An interior member is disposed in the lumen and extends along a length of the inner surface. The interior member is engaged with the inner surface such that a chamber is defined therebetween. A conduit is engaged with the tubular member for transmission of a fluid for selectively varying a dimension of the chamber. An amount of fluid is established in the chamber such that the chamber has a first thickness. The amount of fluid in the chamber is adjusted such that the chamber has a second thickness. A negative pressure is drawn through the proximal end of the tube to draw the body fluid from the body space through the drainage tube.

BRIEF DESCRIPTIONS OF THE DRAWINGS

FIG. 1 illustrates a side view of a tubular drainage device, according to an embodiment of the invention;

FIG. 2A illustrates a longitudinal sectional view of the tubular drainage device of FIG. 1, wherein an inflation fluid has been introduced to define a chamber between the inner surface of the tubular member and an interior member;

FIG. 2B illustrates a longitudinal sectional view of the tubular drainage device as in FIG. 2A, wherein the inflation fluid has been evacuated to collapse the chamber;

FIG. 3A is an enlarged cross-sectional view of the tubular drainage device of FIG. 2A, taken along line 3A-3A;

FIG. 3B is an enlarged cross-sectional view of the tubular drainage device of FIG. 2B, taken along line 3B-3B.

DETAILED DESCRIPTION OF THE DRAWINGS AND THE PRESENTLY PREFERRED EMBODIMENTS

Figure 4:
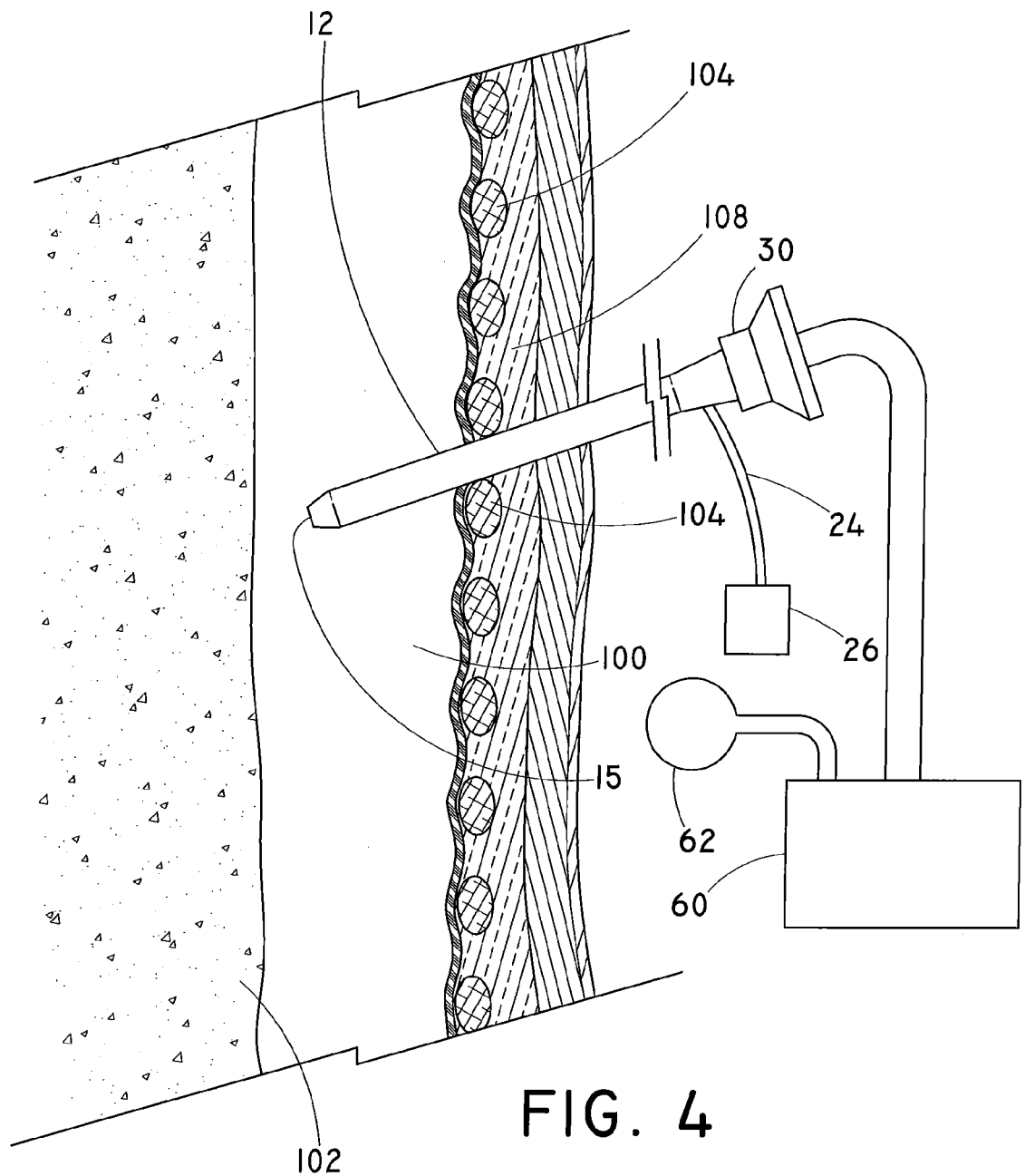
FIG. 4 depicts a tubular drainage device positioned for draining the pleural space of a patient.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Throughout the specification, when referring to a medical device, or a portion of a medical device, the terms "distal" and "distally" shall denote a position, direction, or orientation that is generally toward, or in the direction of, the patient when the device is in use. The terms "proximal" and "proximally" shall denote a position, direction, or orientation that is generally away from the patient, or closer to the operator, during use of the device. It is understood that like-referenced numerals are used throughout the Figures to designate similar components.

The tubular drainage device described herein can be useful for drainage of vessels, lumens, ducts, spaces, or passageways of the body. When discussion of such vessels, lumens, ducts, spaces, or passageways is made herein, these terms are used to describe such structures in general as found in the body of the patient, and are not limited to any one particular vessel, lumen, duct, space, passageway, etc.

In the embodiment shown in the figures, the tubular drainage device comprises a chest tube 10 for draining fluid from the pleural space. As stated above, chest tube 10 is only one example of a tubular drainage device according to the present invention. Those skilled in the art will appreciate that the tubular drainage device as shown and described herein will be suitable for use in draining fluid from other vessels, lumens, ducts, spaces, or passageways in the body, with no more than minor and/or routine modification. Non-limiting additional examples include catheters and surgical drain tubes for draining fluid from other orifices (besides the chest cavity), endotracheal tubes, feeding tubes, gastric tubes, nephrostomy tubes, biliary tubes, and tubes for delivering material to or from the alimentary tract.

With particular reference to the non-limiting embodiment shown in the figures, chest tube 10 comprises a hollow elongated tubular member 12. Hollow elongated tubular member 12 has an exterior surface 32, an inner surface 36, and a lumen 38 extending therethrough. Tubular member 12 has a proximal end 20 and a distal end 14. Preferably, distal end 14 tapers to open distal tip 15. A hub 30 may be affixed at proximal end 20. Hub 30, which may include a Luer connector or other conventional coupling member used in the medical arts, is provided for coupling chest tube 10 to a collection receptacle, such as drainage canister 60. Drainage catheter 60 is shown schematically in FIG. 4.

As shown in FIGS. 2A and 2B, an interior member 40 extends along tubular member inner surface 36. In one embodiment, interior member 40 comprises a thin layer of tubing. Preferably, interior member 40 extends along all, or substantially all, of the circumference of inner surface 36. Interior member 40 includes a proximal end 42 and a distal end 44. Proximal end 42 and distal end 44 are circumferentially bonded to inner surface 36 of tubular member 12 at respective seals 50, 52, to form a substantially air-tight chamber 46 that circumferentially extends between interior member 40 and tubular member inner surface 36. Seals 50, 52 may comprise any conventional mode of engagement between surfaces in common use in the medical arts, such as an adhesive or a thermal bond. One example of a suitable adhesive comprises a LOCTITE® cyanoacrylate adhesive, available from Henkel Corporation.

One end of a conduit 24 extends through an opening in tubular member proximal end 20, and communicates with chamber 46. The other end of conduit 24 communicates with a source 26 of an inflation fluid. The inflation fluid may be any fluid commonly used in the medical arts for inflating an expandable member, such as air or a saline solution. Chamber 46 (FIGS. 2A, 3A) is formed upon the introduction of the inflation fluid into the space between tubular member 12 and interior member 40. FIGS. 2B, 3B illustrate the relative positions of tubular member 12 and interior member 40 prior to introduction of the inflation fluid, and/or following an evacuation of the inflation fluid from the chamber whereby the chamber is collapsed. Inflation fluid may be evacuated from the chamber by any conventional means. If desired, this can conveniently be accomplished by conventional use of a stopcock (not shown) or like device along conduit 24 to create a pathway for communication between a negative pressure source (e.g., a syringe) and the chamber.

Elongated tubular member 12 may be formed of any materials commonly utilized in the art for forming such tubes. For example, tubular member 12 may be formed from a relatively rigid, clear polymer, such as polyvinylchloride (PVC). Those skilled in the art will appreciate that other polymers commonly employed for such purposes, such as polyurethane and polyamide (nylon), may be substituted. Tubular member 12 may have any dimensions typically provided with conventional chest tubes. For example, tubular member 12 may have an outer diameter from about 8 to 36 French (0.11 to 0.47 inch)(2.8 to 12 mm), and an inner diameter from about 0.043 to 0.33 inch (1.10 to 8.4 mm). The tubular member may have a wall thickness of about 0.011 to 0.120 inch (0.28 to 3.05 mm), and may have a length from about 18 to 41 cm. In general, smaller French size chest tubes will have a shorter length, and larger French size tubes will have a greater length.

Interior member 40 may be formed of the same materials used to form tubular member 12, or alternatively, may be formed from expandable polymeric materials commonly used in the medical arts. Typically, interior member 40 will comprise a thin layer of this material, and will have a wall thickness much less than that of the tubular member, such as about 0.002 inch (0.05 mm). Thus, in one example, tubular member 12 may have a wall thickness of about 0.025 inch (0.64 mm), and interior member 40 may have a wall thickness of about 0.002 inch (0.05 mm).

Prior to introduction of an inflation fluid into the chamber, interior member 40 is disposed such that it generally abuts inner surface 36 of tubular member 12, as shown in FIGS. 2B and 3B. In this event, chamber 40 has little, if any, radial thickness. Upon introduction of the inflation fluid into chamber 46 as described herein, interior member 40 and inner surface 36 are spaced to define the chamber 46, as shown in FIGS. 2A and 3A. At this time, chamber 46 may have a radial thickness of, for example, about 0.01 to 0.03 inch (0.25 to 0.76 mm).

Those skilled in the art will appreciate that the dimensions described herein are only examples of suitable dimensions for a chest tube, and that the tubular member, interior member, and chamber may have greater, or lesser, dimensions than specifically described herein. In addition, those skilled in the art will appreciate that tubes intended for use other than as chest drainage tubes will have dimensions appropriate for such intended use. Those skilled in the art are capable of adjusting the dimensions as described herein for such uses, in light of the teachings of the present invention.

As with conventional chest tubes, tubular member 12 may include one or more radiopaque stripes (not shown) along a length of the tubular member. If desired, the tubular member may be provided with a hydrophilic coating along at least the distal portion of its outer surface. Tubular drainage devices are well known in the art, and to the extent not specifically referenced herein, tube 10 may be provided with additional features known to be provided with such tubes.

Chest tube 10 is configured to provide a fluid path from the pleural space to a collection receptacle, such as canister 60 shown in FIG. 4. A vacuum or other negative pressure source 62 can be coupled to the canister to form a closed-suction drainage system. The negative pressure source 62 is configured to create low pressure in the drainage canister 60 in order to draw fluids out of the pleural space and into the drainage canister 60 via chest tube 10 in well-known fashion.

Those skilled in the art will appreciate that the chest tube 10 can be used to facilitate the removal of debris, such as, but not limited to, clots formed of blood, mucus, or other bodily fluids, from within the lumen 38 of tubular member 12. During use of the chest tube, such debris may become adhered to the inner surface of interior member 40, such that it cannot be easily removed by the suction forces generated by the negative pressure source. The presence of such debris in the lumen impedes the flow of fluid to be drained from the body vessel, lumen, duct, space, passageway, etc. Depending upon the size and amount of such debris, fluid flow through the tube may be prevented altogether.

The following discussion will describe the use of tube 10 as a chest tube to drain fluid from the pleural space of a patient, and more particularly, will describe and illustrate use of the features of tube 10 to clear a clot from the lumen of the tube. As noted above, the medical tube need not be a chest tube, and the following example is only intended to describe one possible use of tube 10.

FIG. 4 illustrates chest tube 10 positioned in the pleural space of the patient. Those skilled in the art are aware of numerous suitable methods for introducing the distal end of a chest tube into the pleural space. One such method is described in the incorporated-by-reference U.S. Pat. Publ. No. 2011/0152874.

When properly positioned, distal tip 15 of tubular member 12 extends into the pleural space 100 that separates lung 102 and intercostal muscle 108. As shown in FIG. 4, chest tube 10 is positioned between an adjacent pair of ribs 104. Prior to use, the chest tube may be sutured to the skin of the patient in well-known fashion.

An inflation fluid from source 26 is introduced into chamber 46 via conduit 24 as described. Introduction of a fluid into chamber 46 increases the radial thickness, or diameter, of the chamber. As the thickness of chamber 46 is increased, the effective inner diameter of the chest tube for passage of body fluids is reduced. Compare, e.g., the condition of tubular member 12 in FIGS. 2A and 3A wherein the thickness of chamber 46 is increased, with the condition of the tubular member in FIGS. 2B and 3B, wherein the inflation fluid is evacuated from (or has not yet been introduced into) the chamber. As illustrated, chamber 46 has only a nominal thickness in FIGS. 2B and 3B, thereby increasing the effective inner diameter of the chest tube. In FIGS. 2A and 3A, with chamber 46 inflated to its maximum radial diameter, the effective inner diameter of the chest tube available for passage of body fluid is reduced when compared to FIGS. 2B and 3B.

As discussed above, once a chest tube has been in use for a period of time, debris drained from the pleural space may build up in the passageway through the tube. Build-up of such debris may clog the passageway and prevent further drainage of body fluid therethrough. An example of debris D clogging the passageway of a drainage tube is shown in FIG. 2A.

In order to clear this debris, the inflation fluid is evacuated from the chamber. This action deflates chamber 46, thereby increasing the effective diameter of the chest tube as shown in FIGS. 2B and 3B. As a result of the increased effective diameter of the tube, the clogged debris loosens from its engagement with the surface of the interior member 40, as shown in FIG. 2B. Once loosened from engagement with this surface, the debris may be drawn through the chest tube and into the canister 60 by the suction created by negative pressure source 62. Following removal of the debris, chamber 46 can be reinflated as before, and drainage of fluid from the pleural space is resumed. The process can then be repeated as necessary in the event of future clogging of the lumen.

As an alternative to the method described above, the inflation/deflation sequence of the chamber can be reversed. In this example, the chamber may be in the deflated condition shown in FIGS. 2B, 3B during normal drainage operation. As discussed above, this condition provides a larger effective inner diameter of the tube. If the lumen becomes clogged, the chamber is inflated as described above to the condition shown in FIGS. 2A, 3A to compact the clogging material. Then, the chamber is deflated to its original condition by evacuating the inflation fluid, thereby once again increasing the effective diameter of the lumen. This action is intended to free at least a portion of the compacted material from contact with the inner surface of the interior member 40, and thereby, facilitate removal of the compacted debris by the suction forces as described.

Although it is preferred that interior member 40 extend along virtually the entire inner circumference of inner surface 36 to form the air-tight chamber as shown and described, this is not necessarily required in all embodiments. For example, interior member 40 may extend longitudinally as a strip along all or part of the length of the inner surface, but not necessarily around the entire inner circumference. In this event, the longitudinal strip will be adequately sealed to form the chamber, and the chamber communicates with the source of inflation fluid as described above. As a still further alternative, interior member 40 and chamber 46 need not necessarily extend the entire length of the inner surface of the tubular member. However, it is believed that best results will be achieved when the interior member extends along all, or at least substantially all, of the inner circumference of the inner surface, as shown and described herein.

Drawings in the figures illustrating various embodiments are not necessarily to scale. Some drawings may have certain details magnified for emphasis, and any different numbers or proportions of parts should not be read as limiting, unless so designated in the present disclosure. Those of skill in the art will appreciate that embodiments not expressly described and/or illustrated herein may be practiced within the scope of the present invention. It is therefore intended that the foregoing detailed description be regarded as illustrative rather than limiting. It should be understood that the following claims, including all equivalents, are intended to define the spirit and scope of this invention.

What is claimed is:

1. A medical device for draining a fluid from the body of a patient, comprising: a relatively rigid tubular member configured to have a distal end residing interiorly of the body of a patient and a proximal end extending exteriorly of the body of the patient, said distal end having an opening for transmission of said fluid, the tubular member having an inner surface and extending between said distal end and said proximal end, said inner surface defining a lumen; and an interior member with a diameter and disposed in said lumen and extending along a length of said inner surface, said interior member engaged with said inner surface such that a chamber is defined therebetween; and a conduit engaged with said tubular member for transmission of an inflation fluid for selectively varying a dimension of said chamber; wherein inflation of said chamber increases a radial thickness of said chamber, decreases said diameter of said interior member, and reduces an effective size of said lumen, and deflation of said chamber decreases said radial thickness of said chamber, increases said diameter of said interior member, and increases said effective size of said lumen, wherein said tubular member and said interior member are configured and arranged to controllably vary said radial thickness of said chamber upon selective transmission or said inflation fluid up to a maximum thickness of about 0.03 inch (0.76 mm).

2. The medical device of claim 1, wherein said interior member extends at least substantially the length of said inner surface.

3. The medical device of claim 2, wherein said tubular member inner surface has a circumference, and said interior member extends along the circumference C of said inner surface.

4. The medical device of claim 3, wherein said inner surface has a proximal end and a distal end, further comprising a circumferential seal between said inner surface proximal end and a proximal end of said interior member, and a circumferential seal between said inner surface distal end and a distal end of said interior member.

5. A drainage system comprising: a relatively rigid tubular member configured to have a distal end residing within an interior body space of a patient and a proximal end extending outside of the body of the patient, said distal end having an opening for receiving a body fluid from said body space, the tubular member having an inner surface extending between said distal end and said proximal end, said inner surface defining a lumen; an interior member with a diameter disposed in said lumen and extending along a length of said inner surface, said interior member engaged with said inner surface such that a substantially air-tight chamber is defined therebetween; and a source of an inflation fluid in communication with said chamber; wherein inflation of said chamber increases a radial thickness of said chamber, decreases said diameter of said interior member, and reduces an effective size of said lumen, and deflation of said chamber decreases said radial thickness of said chamber, increases said diameter of said interior member, and increases said effective size of said lumen, wherein the radial thickness of said chamber may be expanded from a nominal thickness prior to transmission of said inflation fluid wherein said interior member substantially abuts said inner surface, to a maximum thickness upon transmission of said inflation fluid into said chamber, said maximum thickness between about 0.01 and 0.03 inch (0.25 and 0.76 mm).

6. The system of claim 5, wherein said interior member extends at least substantially the length of said inner surface.

7. The system of claim 6, wherein said tubular member inner surface has a circumference, and said interior member extends along the circumference of said inner surface.

8. The system of claim 5, further comprising a conduit for transmission of said inflation fluid between said fluid source and said chamber.

9. The system of claim 5, further comprising a collection receptacle for said body fluid, said collection receptacle in communication with the lumen of the tubular member.

10. The system of claim 9, further comprising a negative pressure source for drawing said body fluid into said collection receptacle.

11. The system of claim 10, wherein the negative pressure source comprises a vacuum.

12. A method for draining a body fluid from an interior body space of a patient, comprising: positioning a drainage tube for receiving said body fluid, said drainage tube comprising a relatively rigid tubular member having a distal end residing within said interior body space of the patient and a proximal end extending outside of the body of the patient, the tubular member having an inner surface with a diameter extending between said distal end and said proximal end, said inner surface defining a lumen, an interior member disposed in said lumen and extending along a length of said inner surface, said interior member engaged with said inner surface such that a chamber is defined therebetween, and a conduit engaged with said tubular member for transmission of a fluid for selectively varying a dimension of said chamber; establishing an amount of fluid in said chamber such that said chamber has a first radial thickness; adjusting the amount of fluid in said chamber such that said chamber has a second radial thickness; and drawing a negative pressure through the proximal end of the tube to draw said body fluid from said body space through said drainage tube; wherein inflation of said chamber increases a radial thickness of said chamber, decreases said diameter of said interior member, and reduces an effective size of said lumen and deflation of said chamber decreases said radial thickness of said chamber, increases said diameter of said interior member, and increases said effective size or said lumen, wherein said first radial thickness or said chamber is greater than said second radial thickness, wherein said adjusting step comprises evacuating fluid from said chamber to achieve said chamber second radial thickness, and wherein said first radial thickness is between about 0.01 and 0.03 inch (0.25 and 0.76 mm).

13. The method of claim 12, wherein said first radial thickness is about 0.02 inch (0.51 mm) and said negative pressure draws said body fluid into a collection receptacle.

14. The method of claim 12, wherein said first radial thickness of said chamber is less than said second radial thickness, and wherein said adjusting step comprises introducing said amount of fluid into said chamber to achieve said chamber second radial thickness, said method including the further step of evacuating fluid from said chamber at said second radial thickness prior to said step of drawing said negative pressure.

15. The method of claim 14, wherein said second radial thickness is between about 0.01 and 0.03 inch (0.25 and 0.76 mm).

* * * * *